(12) United States Patent
Van Lier et al.

(10) Patent No.: US 6,328,968 B1
(45) Date of Patent: Dec. 11, 2001

(54) METHODS AND MEANS FOR MODIFYING COMPLEMENT ACTIVATION

(75) Inventors: René Antonius Wilhelmus Van Lier, Uithoorn; Jörg Hamann, Amsterdam, both of (NL)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 0 days.

(21) Appl. No.: 09/242,161
(22) PCT Filed: Aug. 11, 1997
(86) PCT No.: PCT/NL97/00462
§ 371 Date: Jun. 11, 1999
§ 102(e) Date: Jun. 11, 1999
(87) PCT Pub. No.: WO98/06838
PCT Pub. Date: Feb. 19, 1998

(30) Foreign Application Priority Data

Aug. 9, 1996 (EP) .................................................. 96202244

(51) Int. Cl.[7] ............................ A61K 38/36; A61K 38/17
(52) U.S. Cl. ............................................ 424/184.1; 514/12
(58) Field of Search ........................... 530/387.1, 388.25; 424/139.1, 184.1; 435/7.2, 7.8, 69.1; 514/12

(56) References Cited

PUBLICATIONS

Hamann et al. J. Exp. Med. 184:1185–1189, Sep. 1996.*
Brodbeck et al. J. Immunol. 156:2528–2533, Sep. 1996.*
Brodbeck, W. et al., J Immunol. 156:2528–33, 1996.*

* cited by examiner

*Primary Examiner*—David Saunders
*Assistant Examiner*—Amy DeCloux
(74) *Attorney, Agent, or Firm*—Hoffman & Baron, LLP

(57) ABSTRACT

A method for regulating immunological interaction comprising inhibiting the binding between cells bearing CD55 protein and activated leucocytes bearing CD97 protein.

10 Claims, 6 Drawing Sheets

METHODS AND MEANS FOR MODIFYING COMPLEMENT ACTIVATION

This application is a national stage filing under 35 USC 371 from PCT/NL97/00462, filed Aug. 11, 1997, which claims priority to EPO 96202244.8, filed Aug. 9, 1996.

BACKGROUND OF THE INVENTION

The invention relates to the field of immunology, in particular molecular immunology and uses thereof in modern medicine. In particular the invention provides methods and means that find their use in the field of modifying the complement activation cascade and provides methods and means for interference with immune reactions by manipulation of CD97-CD55 interaction".

SUMMARY OF THE INVENTION

The invention provides means and methods to (down) regulate the complement activation pathway and other interactions of the immune system. This is of particular interest in the area of transplantations of organs and/or tissues and/or cells from donors to recipients. To avoid immunologic responses from the host against the transplanted material (the graft) careful matching of the immunological profile of both host and recipient is required. This requirement makes the availability of transplants or grafts a limiting factor in transplantation medicine. It would therefore be a major step forward if this requirement could be avoided so that many more donors become available for transplantation purposes. In working towards a suitable source for transplantable organs and tissues porcine material has been considered. Transplanting porcine material into humans would normally result in an immunogenic reaction, usually a hyperactive rejection of the transplant. For this reason transgenic pigs have been developed which express CD55 decay accelerating factor on the surface of their cells. CD55 plays an important role in complement inactivation as explained below. In short CD55 inhibits two important convertases in the complement activation pathway.

Thus it was thought that by providing the porcine transplant with CD55 the complement activation could be inhibited. It has now been found that the solution for avoiding the hyperimmune rejection may not be that simple, because of the role of the CD97 protein. The present invention identifies that problem and solves it.

Figure 1:
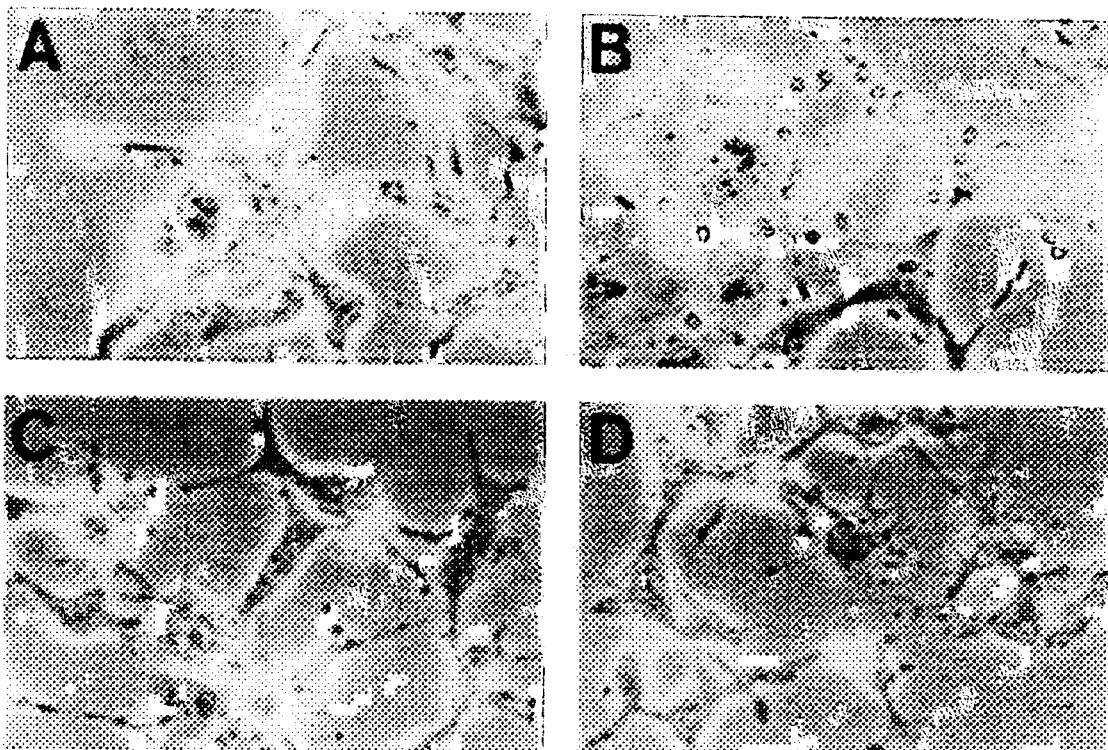
Figure 2:
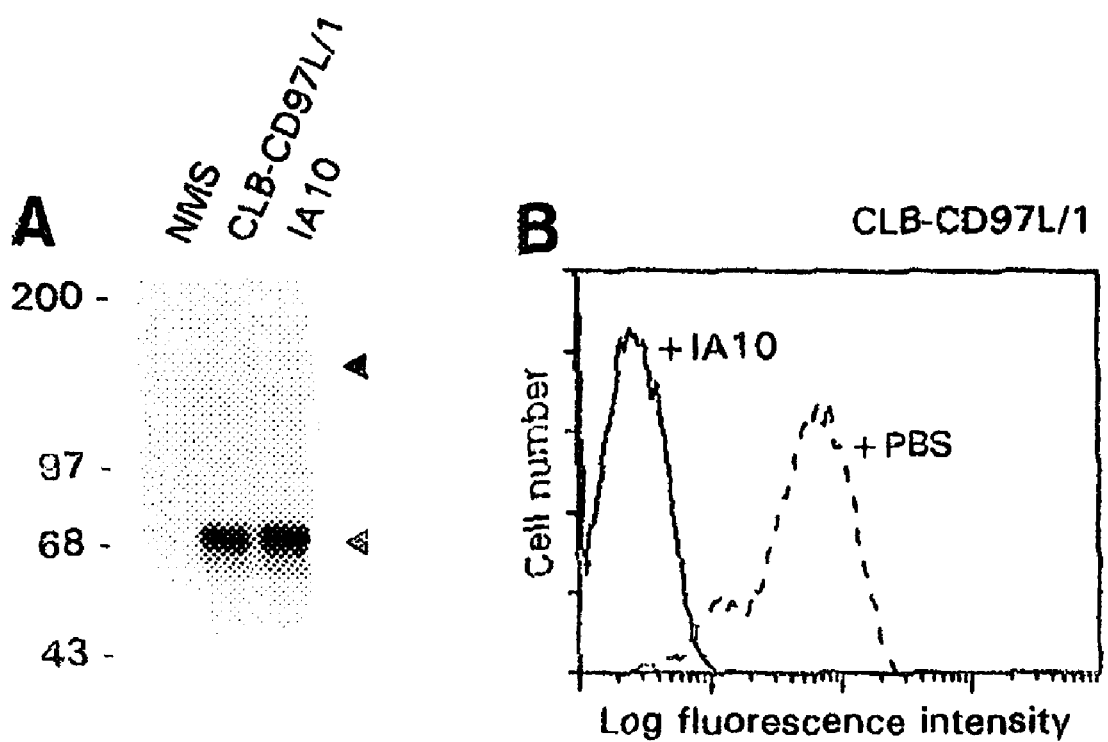
Figure 3:
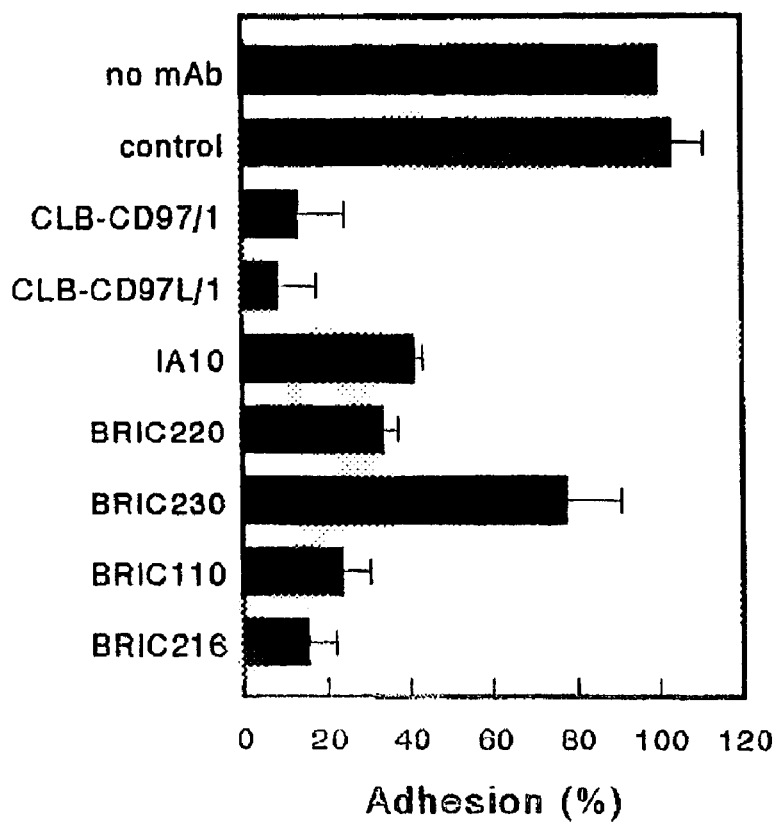

The invention also provides means and methods to regulate early and late interactions that play a role in (auto) immune disease. Autoimmune diseases, such as rheumatoid arthritis, multiple sclerosis, SLE, diabetes and others, are diseases of which the pathogenetic mechanisms are generally not well understood, but whereby a complex of immune reactions as diverse as cytokines activation, activated cells of the immune system, antibody formation and complement activation are alone and in combination directed against "self" components of the patient's body. Such a cascade of immune reactions can lead to a disturbance of the patient's immunological homeostasis which, when not sufficiently mitigated by the body's own system of immune regulation, lead to serious and life threatening disease. Also, acquired immune deficiencies or normal immunologic reactions to infectious agents and the like can lead to a similar immune reaction that is in itself harmful to a patient. CD97 is an antigen which becomes immediately upregulated on most leucocytes during activation (1). We recently identified CD97 as a 7-TM molecule whose membrane-spanning region is homologous to the secretin receptor superfamily (2). CD97 is different from this group of mammalian and insect peptide hormone receptors (3), in that it has an extended extracellular region with three to five EGF domains at the N-terminus. The finding of a highly similar architecture in EMR1 (4), which possesses six EGF domains, and its probable murine homologue F4/80 (5) indicates the existence of a new group of 7-TM receptors characterized by several N-terminal EGF domains. We have demonstrated that this new type of 7-TM molecule has recently evolved by exon shuffling to the upstream region of an ancestral gene from the secretin receptor superfamily (6). All EGF domains in CD97 and EMR1, except the most N-terminal ones, possess a calcium binding site. The $Ca^{2+}$ in this subgroup of EGF domains stabilizes the conformation of the domain and can mediate contact to other proteins (7). The rather recent acquisition of EGF domains raised the possibility that CD97, in parallel with its molecular evolution, has acquired the ability to bind cellular ligands. To explore this, COS cells transfected with CD97 cDNA were incubated with different cells of haematopoietic origin. As shown in FIG. 1, adherence of peripheral blood lymphocytes (PBL) and erythrocytes to COS cells expressing CD97 was observed which was completely abolished by CD97 mAbs CLB-CD97/1 (see the experimental part) or BL-Ac/F2 (1). Once the binding studies indicated that a ligand for CD97 is expressed on erythrocytes, immunization of mice with human erythrocytes was used to generate a ligand-specific mAb. One mAb (CLB-CD97L/1) was identified that blocked the adherence of both, erythrocytes and PBL to CD97-transfected COS cells. This mAb recognizes a 70-kD protein (FIG. 2A). Among antigens of this size studied within the Fifth International Leucocyte Typing Workshop, a small number was found to be expressed by both erythrocytes and lymphocytes (8). When we tested the capacity of mAbs directed against these antigens to block the binding of erythrocytes to CD97 transfectants, IA10, a mAb recognizing CD55 (9) turned out to be inhibitory. A direct comparison of CLB-CD97L/1 with IA10 revealed that both mAbs immunoprecipitate not only the same major protein of 70 kD which characterizes the CD55 antigen (10), but also a minor band at 140 kD which represents dimeric CD55 (11) (FIG. 2A). Furthermore, IA10 completely blocks the binding of biotinylated CLB-CD97L/1 to PBL (FIG. 2B), indicating that the mAb generated to the ligand of CD97 recognizes the same epitope as IA10 that has been previously mapped to the first (of four) SCR of CD55 (12). CD55 or decay accelerating factor (DAF) is a GPI-anchored molecule expressed by all blood cells and cells in contact with blood and tissue fluid that protects from complement-mediated damage by inhibiting C3/C5 convertases (10). To investigate the specificity of the interaction between CD97 and CD55, a larger panel of CD55 mAbs, directed against distinct SCR domains within the molecule, was tested in the above described adherence assay. As shown in FIG. 3, inhibition of erythrocyte adhesion to CD97-transfected COS cells between 23 and 92% was observed. The finding that also mAbs mapping to the second (BRIC110) and third (BRIC216) SCR of CD55 are able to block suggests that these domains in addition to the first SCR are involved in ligation of CD97. The ability to dissociate and prevent assembly of C3/C5 convertases in both the classical and alternative pathway of the complement cascade has recently been mapped to the SCR domains two, three and four (12,13). It was shown that SCR1 is not required for DAF function, but SCR2, SCR3 and SCR4 are each necessary for DAF to exert its protective effect with regard to complement activation. Removal of SCR1 was associated with a small increase in inhibitory activity. The finding that the first SCR of CD55 is involved in adhesion to CD97 is the first demonstration of a molecular function for this domain.

Figure 4:
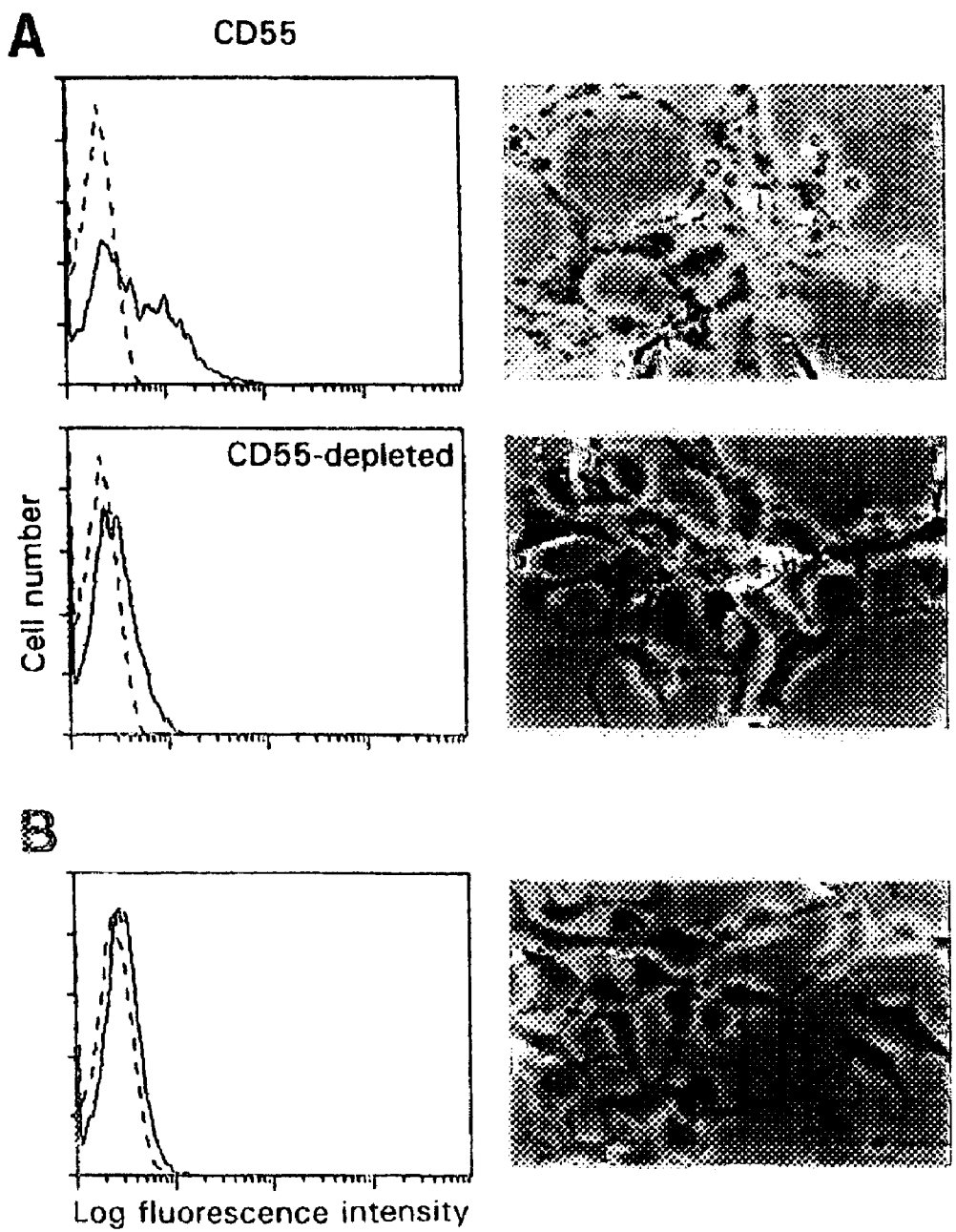
Figure 5:
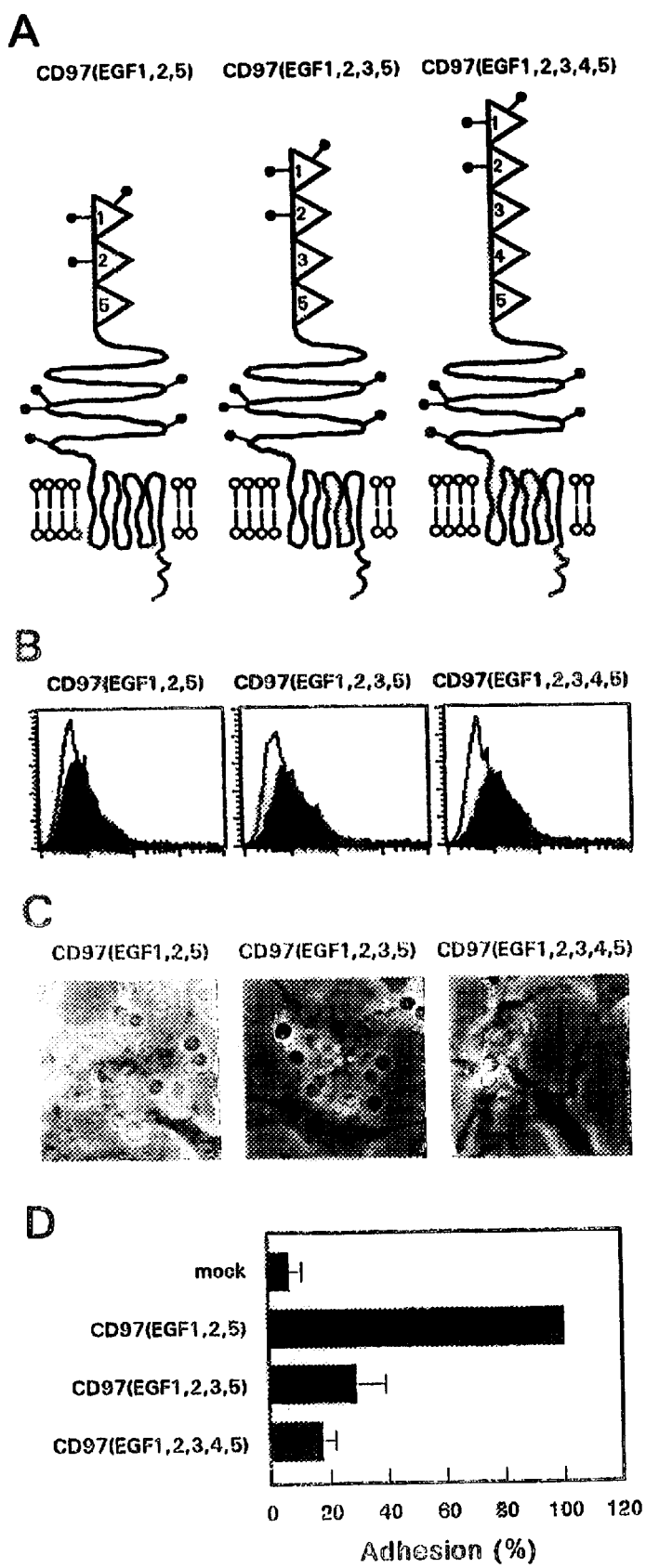
Figure 6:
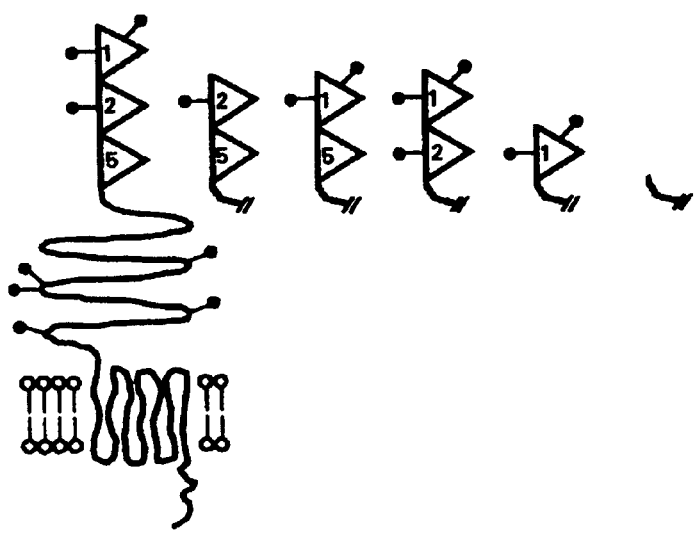

Further evidence that CD97 specifically interacts with CD55 came from the observations that erythrocytes lacking CD55 expression fail to adhere to CD97 transfectants. First, paroxysmal nocturnal hemoglobinuria (PNH) is an acquired somatic defect in GPI-anchor synthesis that leads to the absence of GPI-anchored molecules (14). Due to the clonal character of this hematopoietic stem cell disorder, CD55-positive erythrocytes remain that can adhere to CD97 transfectants. However, after depletion of the unaffected, CD55-expressing erythrocytes, a complete abrogation of adherence was seen (FIG. 4A). Second, the Inab phenotype represents an inherited deficiency in CD55 expression due to truncative mutations in the CD55 gene (15). Erythrocytes with this phenotype were not able to bind to COS cells expressing CD97 (FIG. 4B). Further investigation towards the specificity of the interaction between CD97 and CD55 demonstrated the specific relationship between these molecules. Alternative splicing of EGF domains encoded by the CD97 gene results in isoforms possessing either three (EGF1,2,5), four (EGF1,2,3,5), or five EGF domains (EGF1,2,3,4,5). The initial observation that CD55 is a cellular ligand for CD97 was based on experiments with the isoform CD97 (EGF1,2,5) which contains three EGF domains. To analyze the adhesive capacity of the larger isoforms, the respective cDNAs were cloned and expressed in COS cells. Specific adhesion of erythrocytes to the transfectants demonstrated that all three CD97 isoforms are able to bind CD55 (FIG. 5). However, expression of CD97(EGF1,2,3,5) and CD97 (EGF1,2,3,4,5) resulted in less and smaller rosettes compared with CD97(EGF1,2,5). Identical results were received in binding studies with PBL (data not shown). Quantification of erythrocyte binding to COS cells expressing similar amounts of the different CD97 isoforms confirmed a significantly lower binding capacity of the larger isoforms expressing four and five EGF domains. With respect to the different binding capacity of CD97 isoforms assays are valuable which allow to discriminate between these isoforms. For this we can use various methods, such as domain-specific mAbs or a RT-PCR strategy. To map the binding site of CD97 mAbs, mutant cDNAs were generated which encode CD97 truncated for distinct EGF domains. Since the EGF domains are encoded by individual exons, systematic deletion of the respective exons by SOE-PCR resulted in recombinants designated as CD97-DEGF1, CD97-DEGF2, and CD97-DEGF5. To express the truncated CD97 forms, COS cells were transiently transfected with the mutant cDNAs. Testing the reactivity of a panel of seven CD97 mAbs by flow cytometry revealed that BL-Ac/F2, VIM3, VIM3b, VIM3c, and CLB-CD97/1 are directed to the first EGF domain whereas CLB-CD97/2 and MEM-180 do not bind to one of the EGF domains (FIG. 6). Domain-specific mAbs are generated by standard hybridoma technology from mice immunized with the different CD97 isoforms. As mentioned above, alternative to mAbs nucleic acid based techniques such as RT-PCR are used to detect CD97 isoforms. In RT-PCR specific primers are designed which amplify the alternatively spliced part of the EGF domain region. The 5' primer should be placed within or upstream from the second EGF domain, the 3' primer within or downstream from the fifth EGF domain. CD97 is expressed on activated leucocytes and has a propensity to bind with the autologous CD55 protein, implying attraction of leucocytes (and other inflammatory agents) to autologous tissue, thereby being involved in (auto)immune disease as a consequence of a disturbed humoral (a.o. complement and antibodies) and/or cellular immunological homeostasis. This was studied by determining the expression of CD97 and CD55 in rheumatoid arthritis. Rheumatoid arthritis is a chronic inflammatory disease affecting synovial tissue in multiple joints. The thickened synovial lining layer which characterizes rheumatoid arthritis consists mainly of type A macrophage-like synoviocytes and type B fibroblast-like synoviocytes. As CD55 is a molecule identifying fibroblast-like synoviocytes we investigated the expression of CD97 in the lining layer. A significant expression of CD97 was found on macrophage-like synoviocytes (mean ±SD: 99±1.3%). The expression of CD97 on macrophage-like synoviocytes and of CD55 on fibroblast-like synoviocytes explains the specific architecture of the synovial lining layer which is maintaining and amplifying synovial inflammation. The interaction between the activation-regulated CD97 antigen and CD55 implies the existence of a novel adhesion pathway (16) primarily used by primed but not quiescent leucocytes. The invention provides means and methods to modify, up- or down-regulate this immunological interaction between CD55 and CD97 by blocking of or interfering in the binding of the two molecules, CD97 and CD55. An example of such method and means provided by the invention are antibodies, and their use, specifically directed against the respective binding site of one of the two molecules, such as antibodies corresponding to the CLB-CD97L/1 mAb (deposited at Aug. 7, 1997 at CNCM, Paris under deposit number I-1908.). A preferred embodiment of the invention are humanised antibodies, derived from antibodies such antibodies corresponding to CLB-CD97L/1. Humanisation of antibodies is well known in the art and serves to generate antibodies for use in humans which antibodies are devoid of "non-self" antigens while having maintained the specificity of the binding site. Also, (humanised) idiotype and anti-idiotype antibodies corresponding to and/or derived from antibodies having a specificity directed against the respective binding site of one of the two molecules, such as antibodies corresponding to the CLB-CD97L/1 mAb, are provided by the invention. Furthermore, small blocking peptides, derived as fragment or derivative from said antibodies, or MRUs (molecular recognition units) are also provided by the invention. The invention provides a method to block or interfere with the binding of CD97 and CD55 with the use of such a blocking peptide. However, also other binding or blocking substances, such as peptides (synthetically) derived from such antibodies, or synthetic peptides identified in specific adhesion or blocking assays are also examples of such means and can be used in said method. In addition, synthetic peptides or blocking substances interfering in or antagonising the binding of the two molecules, CD97 and CD55, are derived from amino acid sequences selected from sequences comprising CD97 and/or CD55 molecules, for example from amino acid sequences comprised by the respective binding sites. An example is provided by the EGF1 domain of CD97 or the SCRp1 domain of CD55 where part of the interaction between the two molecules was found to take place. Such peptides or other blocking substances (be it derived from above antibodies or from CD97(-EGF1) and/or CD55(-SCR1) specific amino acid sequences) are obtained by various methods, such as synthetic peptide chemistry and synthetic peptide ELISA (PEPSCAN), utilizing the above antibodies or binding assays testing specific CD97/CD55 interaction. Such peptides are also derived by using a combinatorial phage display library, testing for phages displaying the wanted affinity.

In such a peptide amino acid residues are replaced conventionally, e.g valine can be replaced by alanine (in synthetic peptides all amino acid residues are candidate to conventional replacement with other residues be it D- or L-residues). Also a replacing amino acid is selected by replacement net scanning, or other methods known in the art. Remarkably, among the hundreds of known 7-TM receptors CD97 is the first molecule which has a cellular ligand (17). It needs to be investigated if this is a common feature of the new group of 7-TM receptors with N-terminal EGF domains to which CD97 belongs. Although further physiological consequences of the interaction between CD97 and CD55 remain to be determined, our findings indicate that complement regulation is probably not the exclusive function of CD55. The interaction between CD97 and CD55 also plays a determining role in regulating immunological interaction or homeostasis. The invention provides means (peptides, fragments or derivatives) which can be used to up- or down regulate said homeostasis, thereby providing therapeutic tools or agents allowing for specific regulation of immunological interactions in (auto) immune disease. As a specific example of such disturbed homeostasis CD97/CD55 interaction in rheumatoid arthritis is given, where means down-regulation the inflammatory reaction give great relieve to a patient. Notably, transgenic CD55 is currently being used to downmodulate complement activation by xeno-transplants (18). Our data imply that, although the effect on complement activation might be beneficial for graft survival, attraction of activated leucocytes to the graft would be an unwanted (and so far unanticipated) side-effect of this approach. The invention provides a solution to this problem in that it provides a modified CD55 protein whereby the modification comprises the functional deletion of the first N-terminal short consensus repeat. Preferably this modified protein should be present on a thus modified cell. A most convenient way to generate such cells is to provide them with a vector encoding a modified CD55 protein according to the invention, resulting in a recombinant cell comprising such a vector. Expression of such modified CD55 protein on cells of xeno-transplants will avoid unwanted activation of the immune system via CD97 whereas the complement-regulating activity of CD55 is preserved.

A functional deletion of the first short consensus repeat in the CD55 protein in the context of the present invention means that it looses its binding affinity for CD97 and thus no longer attracts activated leucocytes. Furthermore it is of course important that the CD55 retains its anti-complement activation activity. A modified CD55 protein having these two characteristics is considered to be part of this invention. The target cells for being provided with the modified CD55 are of course cells to be transplanted. These include specifically cells of hematopoietic origin and cells which, in their natural state, are in contact with the blood or lymphatic fluid. Especially non-human mammalian transplantable cells, for instance of porcine origin are contemplated.

When reference is made to recombinant cells comprising a vector, such a vector may be integrated into the cell's genome. This is even preferred. The vector may comprise other elements such as markers, regulatory elements, etc. Apart from modifying the one part of the binding pair it is of course also possible to modify the other side, i.e. CD97. This is also part of the present invention.

Basically the invention provides that any way of suppressing the binding and thus the bringing together of transplanted cells and activated leucocytes will result in a better suppression of complement activation. The invention also provides a method for suppressing complement activation and/or regulation of immunological interaction or homeostasis by inhibiting the binding between CD55 protein and CD97 protein.

As stated before this can be accomplished by functional deletion of the binding domain of either CD97 or CD55 or both, but it may also be accomplished by blocking the binding site of either CD97 or CD55 or both. This blocking can for instance be accomplished using antibodies or fragments thereof or related thereto, such as binding peptides or synthetic peptides blocking the CD55-CD97 interaction. Such blocking substances and derivatives thereof can also be used in a method to inhibit the binding of the two molecules in the treatment of (auto)immune disease.

On the other hand where complement activation is desired, this may also be accomplished resulting in a method for enhancing complement activation whereby (activated) leucocytes are provided with CD55 binding sites derived from CD97.

DETAILED DESCRIPTION OF THE INVENTION

Experimental

Monoclonal Antibodies

CLB-CD97/1 (IgG2a) is a new CD97-specific mAb generated by fusing mouse myeloma SP2/0 with spleen cells from a BALB/c mouse which has been immunized with NIH-3T3 cells stably expressing CD97. CLB-CD97/1 inhibits binding of biotinylated BL-Ac/F2 which indicates that both mAbs are directed to the same CD97 epitope.

The mAb CLB-CD97L/1 (IgG1) was generated by fusing mouse myeloma SP2/0 with spleen cells from a BALB/c mouse immunized with human erythrocytes. Hybridoma supernatants were screened for the capacity to block the adhesion of erythrocytes to COS cells transfected with CD97 (see below) and replated into 96-well culture plates.

Immunoprecipitation and Blocking Studies $^{125}$I-labelled K562 cells were lysed in 1% NP-40 buffer, precleared with mouse normal Ig and incubated with CLB-CD97L/1 and IA10, a CD55 mAb derived from the Fifth International Leucocyte Typing Workshop (12). Immune complexes were adsorbed onto protein A-Sepharose (Pharmacia, Uppsala, Sweden), eluted under reducing conditions, electrophoretically separated by 5 to 15% SDS-PAGE, and visualized by autoradiography.

Blocking of CLB-CD97L/1 by CD55 mAbs was tested by incubation of PBL with IA10 for 20 min prior to staining with biotinylated CLB-CD97L/1, followed by PE-streptavidine. Flow cytometric analysis was done on a FACScan (Becton Dickinson, Mountain View, Calif.).

Adhesion Assays

Binding assays were performed with COS cells three days after transient transfection with CD97 cDNA (2) using lipofectamine (Life Technologies, Inc., Gaithersburg, Md.). Typically, 30% of COS cells expressed CD97, as determined by immunoperoxidase staining with CD97 mAbs. At day one, COS cells were replated into six-well culture plates. Mock-transfection was performed by the same procedure, except that no cDNA was added.

To analyze binding, $10 \times 10^6$ PBL, obtained from human venous blood by isolation on a Percoll density gradient followed by counterflow centrifugal elutriation, or $100 \times 10^6$ erythrocytes were suspended in 1 ml DMEM and overlayed on the COS cells for 30 min at 20° C. Non-adhering cells were removed by gentle washing with PBS prior to examination by microscopy.

For blocking experiments, erythrocytes were labelled with $^{51}$Cr according to manufacturers recommendations (Amersham Co., Buckinghamshire, UK). Binding assays were performed in 12-well culture plates in the presence of 5 μg/ml of mabs. After removing non-adhering cells, the γemission of well contents lysed with 1% Triton X-100 was determined.

Binding of CD55 Deficient Erythrocytes to CD97

Binding of erythrocytes to CD97-transfected COS cells was analyzed as described (see above). To deplete CD55-positive cells from erythrocytes of an PNH patient, cells were incubated with CLB-CD97L/1 prior to addition of saturating amounts of anti-mouse IgG magnetic beads (Dynal, Oslo, Norway) and immunomagnetic selection. Expression of CD55 on the erythrocyte populations was determined by flow cytometry with CLB-CD97L/1 or a subclass control mAb. The Inab phenotype erythrocytes examined in this study are from a new, unpublished case of this extremely rare disorder (Dr. G. Daniels, personal communication).

Epitope Mapping of CD97 mAbs

CD97 cDNAs truncated for distinct EGF domains were produced using the splice-overlap extension polymerase-chain reaction (SOE-PCR) [Horton 89]. Since the EGF domains are encoded by individual exons, the sequences of these exons, separately or in combination, were deleted resulting in mutant cDNAs which encoded the following recombinants: CD97-DEGF1, CD97-DEGF2, and CD97-DEGF5. COS cells were transiently transfected with equal amounts of full-length or mutant CD97 cDNA using lipofectamine (Life Technologies, Inc., Gaithersburg, Md.). Three days after transfection, binding of seven CD97 mAbs was tested by flow cytometric analysis on a FACScan (Becton-Dickinson, Mountain View, Calif.). None of the mAbs stained mock-transfected COS cells.

FIG. 1

Adherence of human PBL (A) and erythrocytes (B) to COS cells expressing CD97 (see above) Both, B and T lymphocytes adhere to CD97-transfected COS cells as revealed from experiments with purified cells (data not shown). No binding is detectable in the presence of CD97 mAbs CLB-CD97/1 (shown) or BL-Ac/F2 (C), or when cells are overlayed on mock-transfected COS cells (D).

FIG. 2

CLB-CD97L/1, a mAb generated to the cellular ligand of CD97 (see above) is specific for CD55. FIG. 2A, CLB-CD97L/1 and the CD55 mAb IA10 immunoprecipitate the same major protein of 70 kD from the erythromyeloid cell line K562 (see above). Notably, also a smaller band at 140 kD that represents dimeric CD55 (11) is detectable in the precipitate from CLB-CD97L/1. The position of molecular size markers in kilodaltons are indicated on the left. FIG. 2B, The binding of biotinylated CLB-CD97L/1 to PBL (dashed line) is completely blocked by the CD55 mAb IA10 (solid line) (see above ).

FIG. 3

CD55 mAbs inhibit the binding of erythrocytes to CD97-transfected COS cells (see the experimental part). Adhesion of $^{51}$Cr-labelled erythrocytes to CD97-transfected COS cells was assessed in the presence of 5 μg/ml of mAbs specific for CD97 (CLB-CD97/1), CD55 (CLB-CD97L/1, IA10, BRIC 220, 230, 110, 216) or a mouse IgG1 control mAb. The CD55 mAbs used are directed to the first (IA10, BRIC220, BRIC230), second (BRIC110) or third (BRIC216) SCR domain (12). Data are expressed as the mean percentage of cell binding (±s.e.m.) from duplicate wells of three independent experiments.

FIG. 4

CD55-deficient erythrocytes are not able to adhere to CD97-transfected COS cells (see the experimental part). FIG. 4A, Erythrocytes from an PNH patient bind to CD97-transfected COS cells (upper right panel) due to the presence of non-effected cells in this clonal disease (14) (upper left panel). After removing the CD55-positive erythrocytes by immunomagnetic sorting (lower left panel), adherence was completely abolished (lower right panel). One representative experiment out of four is shown. FIG. 4B, The complete absence of CD55 expression in the Inab phenotype (15) (left panel) prevents erythrocytes from binding to CD97-transfected COS cells (right panel).

FIG. 5

The three CD97 isoforms have different binding capacities for CD55. FIG. 5A, Schematic structure of the CD97 isoforms possessing three (EGF1,2,5), four (EGF1,2,3,5), or five EGF domains (EGF1,2,3,4,5). FIG. 5B, Immunofluorescence analysis with a panel of CD97 mAbs confirms expression of the CD97 isoforms on tranfected COS cells. Shown is the staining with the CLB-CD97/1 mAb. FIG. 5C, Adherence of erythrocytes to COS cells expressing the three CD97 isoforms. Expression of CD97(EGF1,2,3,5) and CD97(EGF1,2,3,4,5) results in less and smaller rosettes. Mock transfection or the presence of mabs to either CD97 (CLB-CD97/1 or BL-Ac/F2) or CD55 (CLB-CD97L/1) completely prevented adhesion (data not shown). FIG. 5D, Erythrocytes bind with different affinity to COS cells expressing equal amounts of the three CD97 isoforms. Results are expressed as the percent of erythrocyte binding, relative to CD97(EGF1,2,5). Data shown are mean ±SD of duplicate determinations in three independent experiments.

FIG. 6

Epitope mapping of CD97 mAbs. FIG. 6A, Schematic structure of the CD97-DEGF recombinants. Systematic deletion of the EGF domains was undertaken through deletion of the encoding exons by SOE-PCR. FIG. 6B, Immunofluorescence analysis with a panel of CD97 mAbs confirms expression of the CD97-DEGF recombinants in tranfected COS cells. The staining pattern correlates with binding of the mAbs to either the first EGF domain or outside the EGF domains.

REFERENCES

1. W. Eichler, G. Aust, D. Hamann, Scand. J. Immunol. 39, 111 (1994).
2. J. Hamann et al., J. Immunol. 155, 1942 (1995).
3. T. Ishihara et al., EMBO J. 10, 1635 (1991); G. V. Segre and S. R. Goldring, Trends Endocrinol. Metab. 4, 309 (1993).
4. V. Baud et al., Genomics 26, 334 (1995).
5. A. J. McKnight et al., J. Biol. Chem. 271, 486 (1996).
6. J. Hamann, E. Hartmann, R. A. W. van Lier, Genomics 32, 144 (1996).
7. Z. Rao et al., Cell 82, 131 (1995).
8. S. F. Schlossman et al., Eds., Leucocyte Typing V (Oxford University Press, Oxford, 1995).
9. T. Kinoshita, M. E. Medof, R. Silber, V. Nussenzweig, J. Exp. Med. 162, 75 (1985).
10. D. M. Lublin and J. P. Atkinson, Ann. Rev. Immunol. 7, 35 (1989).

11. M. W. Nickells, J. I. Alvarez, D. M. Lublin, J. P. Atkinson, *J. Immunol.* 152, 676 (1994).
12. K. E. Coyne et al., *J. Immunol.* 149, 2906 (1992).
13. W. G. Brodbeck, D. Liu, J. Sperry, C. Mold, M. E. Medof, *J. Immunol.* 156, 2528 (1996).
14. T. Kinoshita, N. Inoue, J. Takeda, *Adv. Immunol.* 60, 57 (1995); L. Luzzatto, M. Bessler, *Curr. Opin. Hematol.* 3, 101 (1996).
15. D. M. Lublin et al., Blood 84, 1276 (1994); G. Daniels, *Human Blood Groups* (Blackwell Science, Oxford, 1995).
16. T. A. Springer, *Cell* 76, 301 (1994).
17. J. M. Baldwin, *EMBO J.* 12, 1693 (1993); S. Watson and S. Arkinstall, *The G-Protein Linked Receptor FactsBook* (Academic Press, London, 1994); T. P. Iismaa, T. J. Biden, J. Shine, *G Protein-Coupled Receptors* (R. G. Landes Co., Austin, 1995).
18. K. R. McCurry et al., *Nature Med.* 1, 423 (1995).
19. J. Gray et al., *J. Immunol.* 157, 5438 (1996)

What is claimed is:

1. A method for regulating immunological interaction comprising inhibiting binding between cells bearing CD55 protein and activated leucocytes bearing CD97 protein by inhibiting the binding between CD55 protein and CD97 protein, whereby the inhibition of the binding regulates the immunological interaction.

2. A method according to claim 1 whereby the inhibition is accomplished by functional deletion of the binding domain of CD55.

3. A method according to claim 1 whereby the inhibition is accomplished by blocking the binding site of either CD97 or CD55 or both.

4. A method according to claim 3 whereby the blocking is accomplished using a synthetic peptide inhibiting interaction between CD55 and CD97.

5. A method according to claim 4 whereby the peptide is derived from an amino acid sequence comprising a CD55 and/or CD97 sequence.

6. A method according to claim 5 whereby the peptide is derived from an amino acid sequence comprising a CD55-SCR1 sequence and/or from an amino acid sequence comprising a CD97-EGF1 sequence.

7. A method according to claim 3 whereby the blocking is accomplished using an antibody.

8. A method according to claim 7 whereby the blocking is accomplished by the antibody CLB-CD97/1, deposited on Aug. 7, 1997 at CDCM, Paris, under deposit number I-908.

9. A method according to claim 8 whereby the antibody is humanised.

10. A method according to claim 7 whereby the blocking is accomplished using a synthetic peptide derived from the antibody CLB-CD97/1, deposited on Aug. 7, 1997 at CNCM, Paris, under deposit number I-1908.

* * * * *